United States Patent
Litvak et al.

(10) Patent No.: US 9,693,698 B2
(45) Date of Patent: Jul. 4, 2017

(54) ELECTROMYOGRAPHY RESPONSE DETECTION SYSTEMS AND METHODS

(75) Inventors: Leonid M. Litvak, Los Angeles, CA (US); William L. Johnson, Santa Clarita, CA (US)

(73) Assignee: Advanced Bionics AG, Staefa (CH)

( * ) Notice: Subject to any disclaimer, the term of this patent is extended or adjusted under 35 U.S.C. 154(b) by 124 days.

(21) Appl. No.: 14/397,461

(22) PCT Filed: May 1, 2012

(86) PCT No.: PCT/US2012/035979
§ 371 (c)(1),
(2), (4) Date: Oct. 27, 2014

(87) PCT Pub. No.: WO2013/165395
PCT Pub. Date: Nov. 7, 2013

(65) Prior Publication Data
US 2015/0088025 A1    Mar. 26, 2015

(51) Int. Cl.
*A61B 5/04* (2006.01)
*A61B 5/0488* (2006.01)
(Continued)

(52) U.S. Cl.
CPC ........ *A61B 5/04012* (2013.01); *A61B 5/0488* (2013.01); *A61B 5/6817* (2013.01);
(Continued)

(58) Field of Classification Search
CPC .......................... A61B 5/04012; A61B 5/0488
See application file for complete search history.

(56) References Cited

U.S. PATENT DOCUMENTS

| 6,224,549 B1 * | 5/2001 | Drongelen | A61B 5/00 600/300 |
| 2005/0085743 A1 * | 4/2005 | Hacker | A61B 5/04001 600/554 |

(Continued)

FOREIGN PATENT DOCUMENTS

WO    WO-97/48447    12/1997

OTHER PUBLICATIONS

International Search Report and Written Opinion received in International Application No. PCT/US12/035979, dated Jan. 23, 2013.
(Continued)

*Primary Examiner* — Michael C Stout
*Assistant Examiner* — Nicholas E Kolderman
(74) *Attorney, Agent, or Firm* — ALG Intellectual Property, LLC

(57) ABSTRACT

An exemplary EMG response detection system may be configured to 1) direct an implantable stimulator to sequentially present a plurality of substantially identical stimulation events to a patient, 2) record a plurality of EMG signals generated by a muscle in the patient and each corresponding to a presentation of a particular stimulation event included in the plurality of substantially identical stimulation events, 3) determine an asynchronous component of each of the recorded EMG signals, and 4) utilize the asynchronous components of the recorded EMG signals to determine whether an EMG response is evoked by the stimulation events.

20 Claims, 12 Drawing Sheets

(51) Int. Cl.
    *A61B 5/00*     (2006.01)
    *A61B 5/12*     (2006.01)
    *A61N 1/36*     (2006.01)

(52) U.S. Cl.
    CPC ............. *A61B 5/121* (2013.01); *A61B 5/7264* (2013.01); *A61N 1/36032* (2013.01)

(56) References Cited

U.S. PATENT DOCUMENTS

2007/0255344 A1    11/2007   van Dijk
2008/0221640 A1*    9/2008   Overstreet ......... A61N 1/37247
                                                              607/48
2009/0259277 A1    10/2009   Cornejo Cruz et al.

OTHER PUBLICATIONS

Clement, Ryan S., et al., *Measuring the Electrical Stapedius Reflex with Stapedius Muscle Electromyogram Recordings, Annals of Biomedical Engineering*, vol. 30, pp. 169-179, Biomedical Engineering Society, USA, (2002),(Methods pp. 170-172).

* cited by examiner

ELECTROMYOGRAPHY RESPONSE DETECTION SYSTEMS AND METHODS

BACKGROUND INFORMATION

Electromyography ("EMG") is a technique for evaluating and recording the electrical activity produced by muscles within the body. Such electrical activity (also referred to as an "EMG response") may be produced in response to application of a stimulation event (e.g., an electrical stimulation pulse train) to the muscle and/or to some other bodily structure neurologically associated with the muscle, and, in some instances, may be characterized by involuntary movement of the muscle in response to the stimulation event. EMG responses may be analyzed to set one or more control parameters governing an operation of an implantable stimulator, detect medical abnormalities, determine activation levels, and/or perform a variety of other medically related tasks associated with a patient.

To illustrate, EMG responses generated by the stapedius muscle are often referred to as "stapedius reflexes" and may be used to objectively determine one or more most comfortable current levels ("M levels") for a cochlear implant patient. An M level refers to a stimulation current level applied by a cochlear implant system at which the patient is most comfortable. For example, a current level of electrical stimulation applied by a cochlear implant system to a patient may be increased until a stapedius reflex (i.e., an involuntary contraction of the stapedius muscle) is elicited. The current level required to elicit a stapedius reflex within the patient (referred to herein as a "stapedius reflex threshold") may then be used by a clinician as a starting point for determining an M level corresponding to the patient.

Unfortunately, some types of EMG responses (e.g., stapedius reflexes) are often difficult to detect. For example, some EMG responses have relatively low signal levels, and can therefore be difficult to distinguish from noise and stimulus artifacts that may be present in a recorded EMG signal that contains an EMG response.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Electromyography ("EMG") response detection systems and methods are described herein. As will be described below, the systems and methods may facilitate detection of an EMG response (e.g., a stapedius reflex) produced by presentation (e.g., application) of one or more stimulation events to the patient by an implantable stimulator (e.g., a cochlear implant), even if the EMG response is masked by noise and/or stimulus artifacts associated with the implantable stimulator and/or the one or more stimulation events.

For example, an exemplary EMG response detection system may be configured to 1) direct an implantable stimulator to sequentially present a plurality of substantially identical stimulation events to a patient, 2) record a plurality of EMG signals generated by a muscle in the patient and each corresponding to a presentation of a particular stimulation event included in the plurality of substantially identical stimulation events, 3) determine an asynchronous component of each of the recorded EMG signals, and 4) utilize the asynchronous components of the recorded EMG signals to determine whether an EMG response (i.e., one or more EMG responses) is evoked by the stimulation events.

As another example, an exemplary EMG response detection system may be configured to 1) direct an implantable stimulator to sequentially present a plurality of substantially identical stimulation events to a patient, 2) record a plurality of EMG signals generated by a muscle in the patient and each corresponding to a presentation of a particular stimulation event included in the plurality of substantially identical stimulation events, 3) determine an averaged EMG signal (i.e., a synchronous component of each of the recorded EMG signals) by averaging each of the recorded EMG signals together, 4) determine whether one or more peaks within the averaged EMG signal are above a predetermined threshold level, and 5) determine, based on the determination of whether one or more peaks within the averaged EMG are above the predetermined threshold level, whether an EMG response (i.e., one or more EMG responses) is evoked by the stimulation events.

Hence, as will be described in more detail below, the determination as to whether a particular stimulation event evokes an EMG response may be made by recording a plurality of EMG signals corresponding to sequential presentations of the stimulation event and then analyzing the synchronous components of the recorded EMG signals or the asynchronous components of the recorded EMG signals. As used herein, a "synchronous component" of a recorded EMG signal refers to a component of the recorded EMG signal that is synchronized with the presentation of the EMG signal's corresponding stimulation event. Likewise, an "asynchronous component" of a recorded EMG signal refers to a component of the recorded EMG signal that is unsynchronized with the presentation of the EMG signal's corresponding stimulation event.

Figure 1:
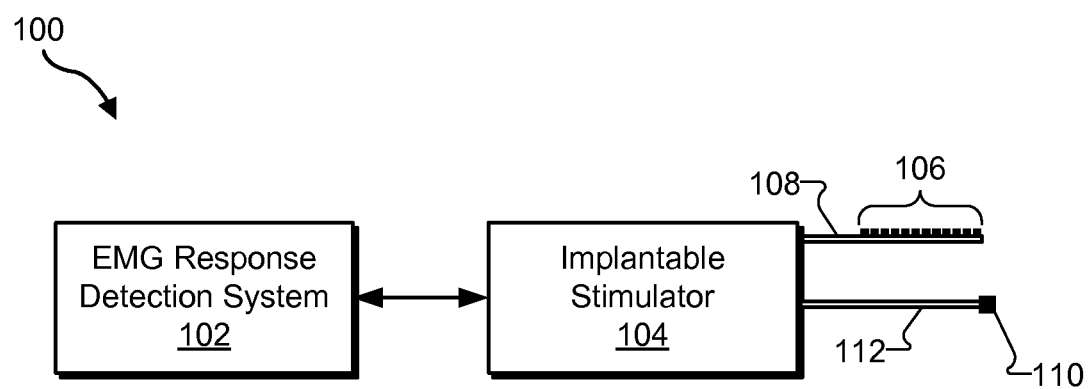
FIG. 1 illustrates an exemplary configuration in which an EMG response detection system is communicatively coupled to an implantable stimulator according to principles described herein.

FIG. 1 illustrates an exemplary configuration 100 in which an EMG response detection system 102 is communicatively coupled to an implantable stimulator 104. EMG response system 102 and implantable stimulator 104 may be communicatively coupled in any suitable manner. For example, EMG response system 102 may be communicatively coupled to implantable stimulator 104 by way of one or more wireless and/or wired communication channels.

EMG response detection system 102 may be configured to detect one or more EMG responses that may be elicited within a patient in response to a presentation of one or more stimulation events to one or more locations within the patient by implantable stimulator 104. EMG response detection system 102 may be implemented by any suitable combination of computing devices, processors, and/or other devices. For example, EMG response detection system 102 may be implemented by one or more fitting devices, electromyographs, and/or sound processors (e.g., a sound processor included in a cochlear implant system). EMG response detection system 102 will be described in more detail below.

Implantable stimulator 104 may be implemented by an auditory prosthesis (e.g., a cochlear implant, a brainstem implant, etc.), a spinal cord stimulator, a neural stimulator, a muscle stimulator, and/or any other stimulation device that may be implanted (e.g., fully implanted) within a patient. In some examples, implantable stimulator 104 may be configured to apply one or more stimulation events to one or more stimulation sites within the patient by way of one or more electrodes 106 disposed on a lead 108 that is coupled to implantable stimulator 104. The one or more stimulation events may include any suitable electrical stimuli as may serve a particular implementation. For example, as will be described in more detail below, the one or more stimulation events may include one or more electrical stimulation pulse trains. In some embodiments, the one or more stimulation events may additionally or alternatively include one or more acoustic, optical, and/or mechanical stimulation events as may serve a particular implementation. The one or more stimulation events applied by implantable stimulator 104 may elicit one or more EMG responses if the one or more stimulation events are of sufficient strength (e.g., if the one or more stimulation events have a high enough intensity level or amplitude).

In some examples, as shown in FIG. 1, a recording electrode 110 disposed on a lead 112 may be communicatively coupled to implantable stimulator 104. Recording electrode 110 may be positioned within the patient such that it is in physical communication with (e.g., implanted within) a muscle within the patient. In this configuration, recording electrode 110 may be used to detect EMG activity (e.g. one or more EMG signals that may include one or more EMG responses). For example, recording electrode 110 may be inserted within the stapedius muscle and used to detect stapedius muscle activity, which may include one or more stapedius reflexes. Alternatively, recording electrode 110 may be in physical communication with any other muscle within the body of a patient. Although recording electrode 110 is shown to be communicatively coupled to implantable stimulator 104, it will be recognized that recording electrode 110 may alternatively be coupled directly to EMG response detection system 102 and/or otherwise implemented.

Figure 2:
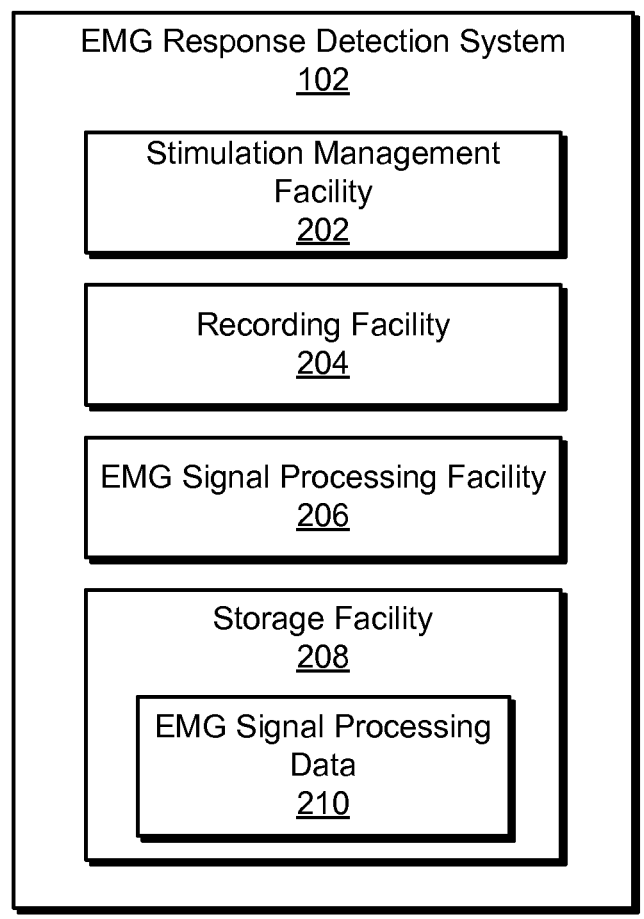
FIG. 2 shows various components of the EMG response detection system shown in FIG. 1 according to principles described herein.

FIG. 2 shows various components of EMG response detection system 102. As shown, EMG response detection system 102 may include, without limitation, a stimulation management facility 202, a recording facility 204, an EMG signal processing facility 206, and a storage facility 208 communicatively coupled to one another. It will be recognized that although facilities 202-208 are shown to be separate facilities in FIG. 2, any of facilities 202-208 may be combined into fewer facilities, such as into a single facility, or divided into more facilities as may serve a particular implementation.

Stimulation management facility 202 may be configured to perform one or more stimulation management operations. For example, in order to determine whether a particular stimulation event elicits an EMG response from a muscle within a patient, stimulation management facility 202 may direct an implantable stimulator (e.g., implantable stimulator 104) to sequentially present substantially identical replicas of the stimulation event to the patient. In other words, stimulation management facility 202 may direct the implantable stimulator to repeatedly present or apply the same stimulation event to the patient a predetermined number of times (e.g., 10 times). By repeatedly applying the same stimulation event to the patient, EMG response detection system 102 may ensure that an EMG response is actually elicited by the stimulation event, as will be described in more detail below.

Figure 3:
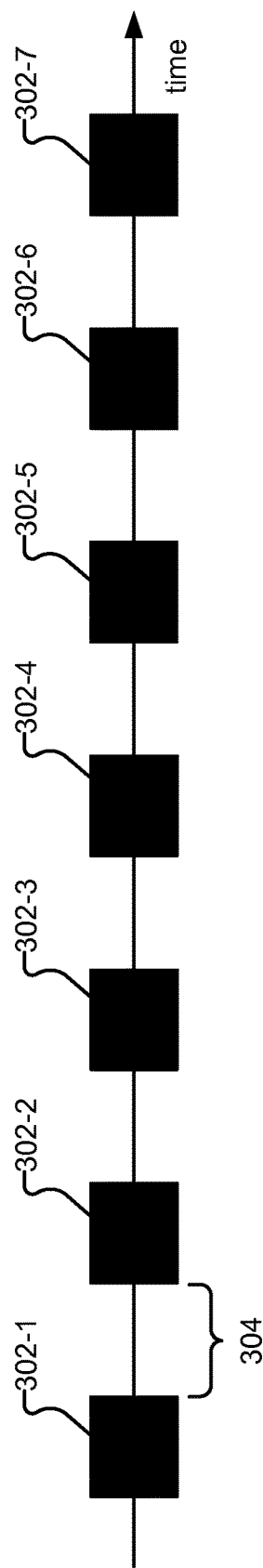
FIG. 3 illustrates a sequential presentation of a plurality of substantially identical stimulation events according to principles described herein.

To illustrate, FIG. 3 illustrates a sequential presentation of a plurality of substantially identical stimulation events 302 (e.g., stimulation events 302-1 through 302-7) by an implantable stimulator at the direction of stimulation management facility 202. While FIG. 3 shows a presentation of seven stimulation events 302, it will be recognized that stimulation management facility 202 may direct the implantable stimulator to sequentially present any number of substantially identical stimulation events 302.

As shown, each stimulation event 302 is temporally spaced one from another by a predetermined time period (e.g., time period 304). As will be described below, this temporal spacing may allow EMG response detection system 102 to record an EMG signal corresponding to each stimulation event 302. The duration of each stimulation event 302, as well as the predetermined time period in between each stimulation event 302, may have any suitable value as may serve a particular implementation. For example, each stimulation event 302 may have a duration of 500 milliseconds ("ms") and may be separated one from another by a predetermined time period of 250 ms. In some alternative examples, each stimulation event 302 may be temporally spaced one from another by predetermined time periods of different durations.

Each stimulation event 302 may include any type of stimulation as may serve a particular implementation. For example, each stimulation event may include any combination of monopolar stimulation, multipolar (e.g., bipolar) stimulation, and/or any other type of stimulation as may serve a particular implementation. In some examples, each stimulation event may include an electrical stimulation pulse train that includes a plurality of stimulation pulses each having any suitable pulse width (e.g., 214 microseconds ("μs")). Other types of stimulation events (e.g., acoustic and/or optical stimulation events) may be used in connection with the systems and methods described herein as may serve a particular implementation.

Stimulation management facility 202 may direct the implantable stimulator to sequentially present the substantially identical stimulation events 302 to a patient in any suitable manner. For example, stimulation management facility 202 may transmit a command to a sound processor (e.g., a sound processor included in a cochlear implant system) in communication with the implantable stimulator directing the sound processor to direct the implantable stimulator to apply the stimulation events 302 by way of one or more electrodes (e.g., electrodes 106) disposed within the patient (e.g., disposed within the cochlea of the patient).

Returning to FIG. 2, recording facility 204 may be configured to record a plurality of EMG signals generated by a muscle in the patient and each corresponding to a presentation of a particular stimulation event included in the plurality of substantially identical stimulation events presented by the implantable stimulator at the direction of stimulation management facility 202. For example, with reference to FIG. 3, recording facility 204 may record seven EMG signals each corresponding to a distinct stimulation event 302.

Figure 4:
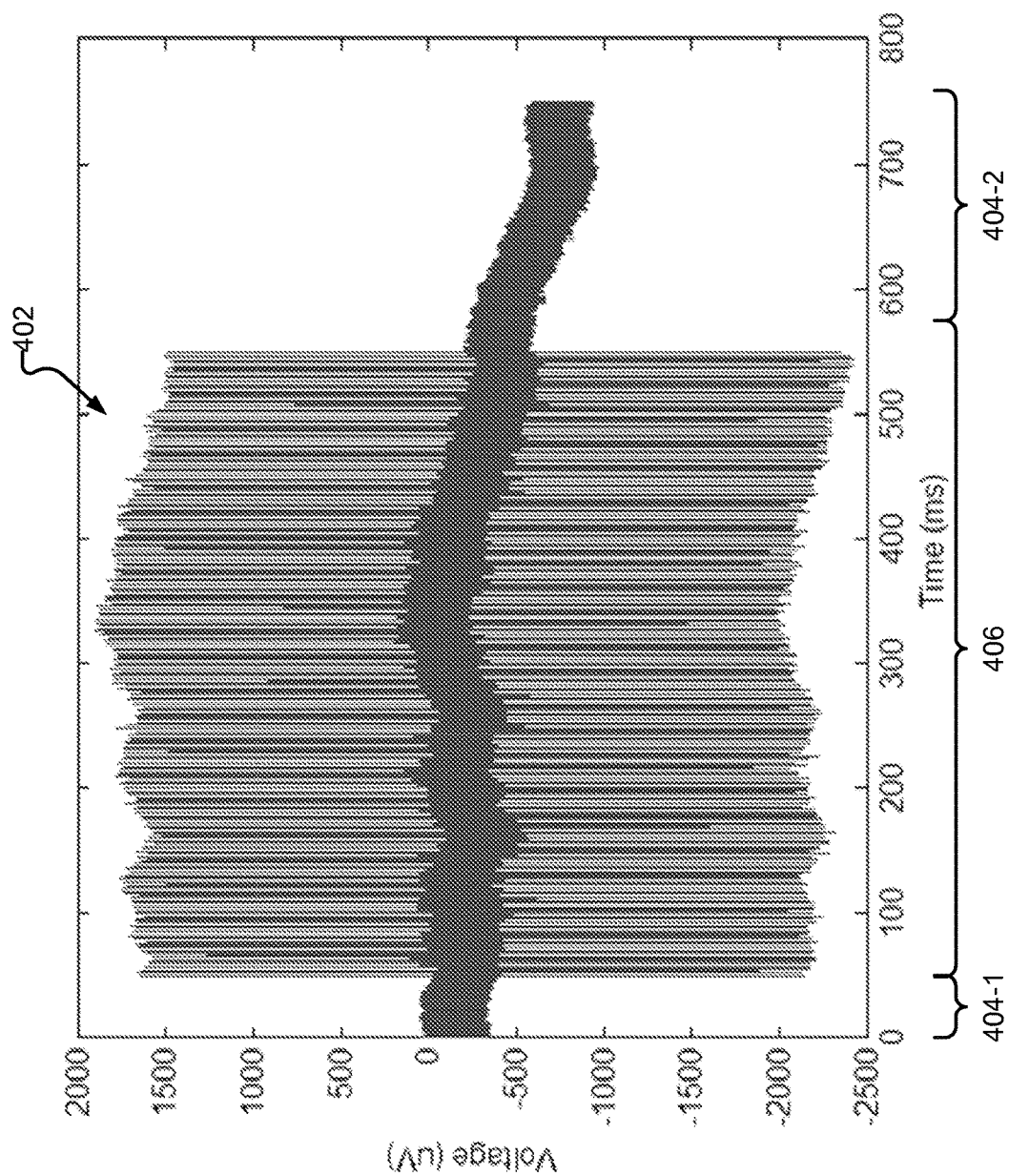
FIG. 4 shows an exemplary EMG signal according to principles described herein.

FIG. 4 shows an exemplary EMG signal 402 that may be recorded by recording facility 204 and that may correspond to a presentation of a particular stimulation event (e.g., stimulation event 302-1). In this example, the stimulation event corresponding to EMG signal 402 has a duration of 500 ms and begins at time equals 50 ms. However, as shown in FIG. 4, recording facility 204 may begin recording EMG signal 402 a predetermined amount of time prior to the presentation of the stimulation event and end recording EMG signal 402 a predetermined amount of time subsequent to the presentation of the stimulation event.

In some examples, EMG signal 402 may be divided into two phases—a baseline phase 404 (e.g., phases 404-1 and 404-2) and a response phase 406. The baseline phase 404 corresponds to a time period during which an occurrence of an EMG response in response to the presentation of the stimulation event is not possible. For example, the baseline phase 404 may include a time period that occurs prior to the presentation of the stimulation event (i.e., phase 404-1) and/or a time period that begins a predetermined amount of time subsequent to the presentation of the stimulation event (i.e., phase 404-2). The response phase 406 corresponds to a time period during which an occurrence of an EMG response in response to the stimulation event is possible. For example, the response phase 406 may begin at the same time (or shortly thereafter) that the presentation of the stimulation event begins and may end a predetermined amount of time after the presentation of the stimulation event ends. As will be described below, the energy contained in an asynchronous component of the EMG signal 402 during the baseline phase 404 and during the response phase 406 may be compared in order to determine whether the EMG signal 402 includes an EMG response or whether the EMG signal 402 only includes noise and/or stimulus artifacts.

As mentioned, EMG signal 402 may include an EMG response elicited by the stimulation event if the stimulation event is of sufficient strength or amplitude. Unfortunately, however, EMG signal 402 may also include noise and stimulus artifacts. As used herein, "noise" refers to any signal that is not correlated with the stimulation event and may be caused by implanted electronics, bodily functions, etc. "Stimulus artifacts" include signals, other than the EMG is response, that are correlated with the stimulation event. For example, stimulus artifacts may include the voltage potential of the stimulation event itself. Another source of stimulus artifacts is cross-talk between the recording circuitry and the stimulation circuitry implanted within the patient.

In some cases, an EMG response included in EMG signal 402 may be masked by noise and/or stimulus artifacts also included in EMG signal 402. For example, the EMG response may have a relatively low intensity level that is beneath the noise floor. In this case, direct analysis of EMG signal 402 may not be able to determine whether EMG signal 402 actually includes an EMG response. Hence, as will be described below, EMG signal 402 may be broken into its synchronous and asynchronous components, either of which may be used to determine whether EMG signal 402 includes an EMG response.

Returning to FIG. 2, EMG signal processing facility 206 may be configured to perform one or more processing operations on the EMG signals recorded by recording facility 204. For example, EMG signal processing facility 206 may determine synchronous and asynchronous components of each of the recorded EMG signal. The synchronous and/or asynchronous components may then be used to determine whether an EMG response is evoked by the stimulation events corresponding to the EMG signals. In other words, the synchronous and/or asynchronous components may be analyzed to determine whether the recorded EMG signals include EMG responses.

In some examples, EMG signal processing facility 206 may determine the synchronous components of the recorded EMG signals by averaging each of the recorded EMG signals together. By so doing, portions of the EMG signals that are not synchronized with each other are minimized. The resulting averaged EMG signal is therefore representative of each of the synchronous components of the recorded EMG signals. In other words, the averaged EMG signal represents a synchronous component common to each of the EMG signals.

Figure 5:
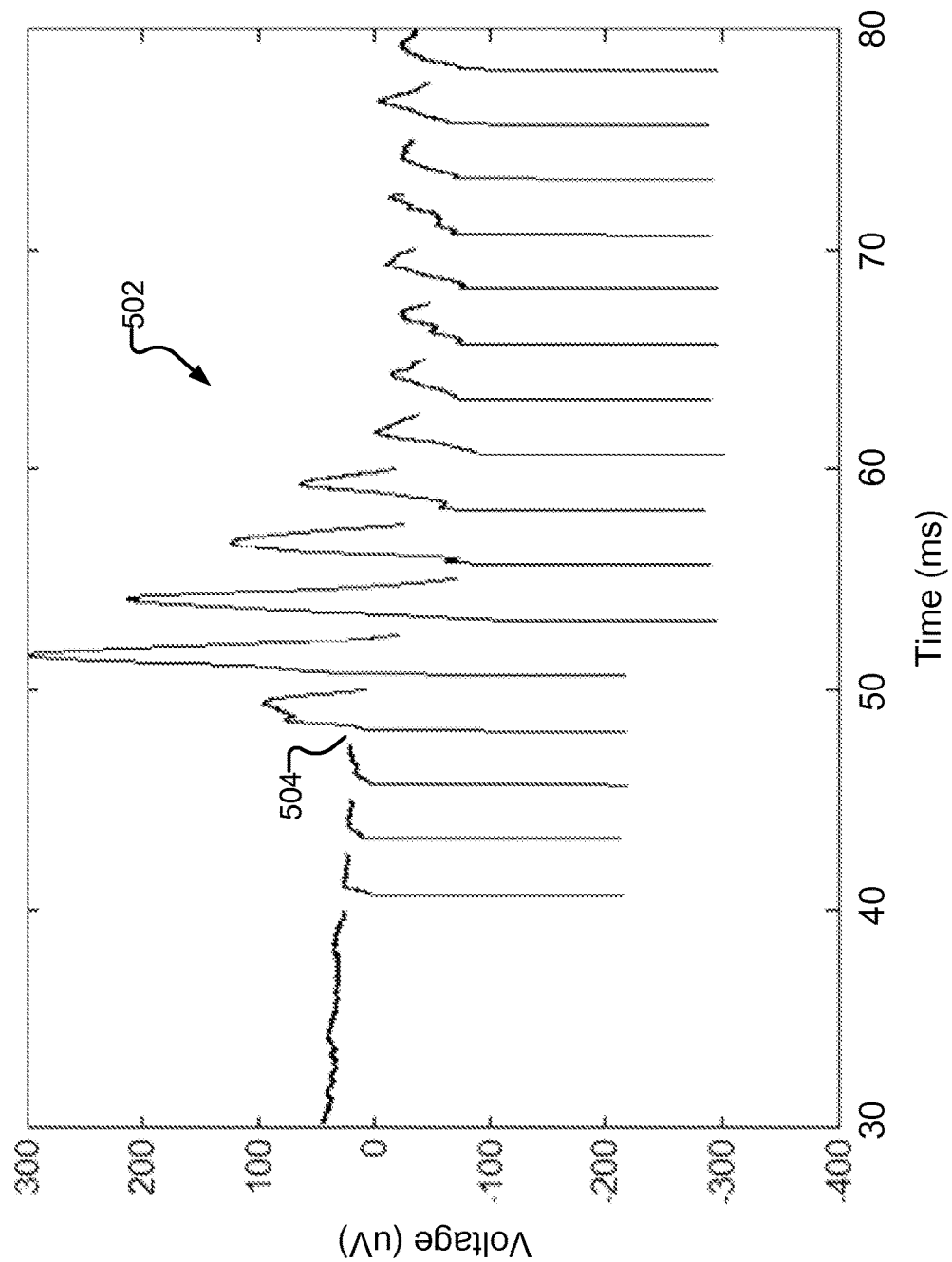
FIG. 5 shows an exemplary averaged EMG signal according to principles described herein.

To illustrate, FIG. 5 shows an exemplary averaged EMG signal 502 that is representative of a synchronous component common to each of a plurality of EMG signals. For example, averaged EMG signal 502 may be representative of a synchronous component of EMG signal 402. It will be recognized that the time scale of averaged EMG signal 502 has been zoomed in compared to the time scale of EMG signal 402 in order to show individual peaks (also referred to as "spikes") that may be included within averaged EMG signal 502. As shown in FIG. 5, averaged EMG signal 502 may include a number of gaps (e.g., gap 504) in between successive peaks. These gaps temporally correlate with individual stimulation pulses included in the stimulation events corresponding to the recorded EMG signals and represent portions of averaged EMG signal 502 that have been zeroed out to account for stimulus artifacts that occur in response to the presentation of the individual stimulation pulses.

In some examples, averaged EMG signal 502 may be used by EMG signal processing facility 206 to determine whether an EMG response is evoked by the stimulation events corresponding to the EMG signals that have been averaged. For example, EMG signal processing facility 206 may determine whether one or more peaks within the averaged EMG signal 502 are above a predetermined threshold level. Based on this determination, EMG signal processing facility 206 may determine whether an EMG response is evoked by the stimulation events.

Figure 6:
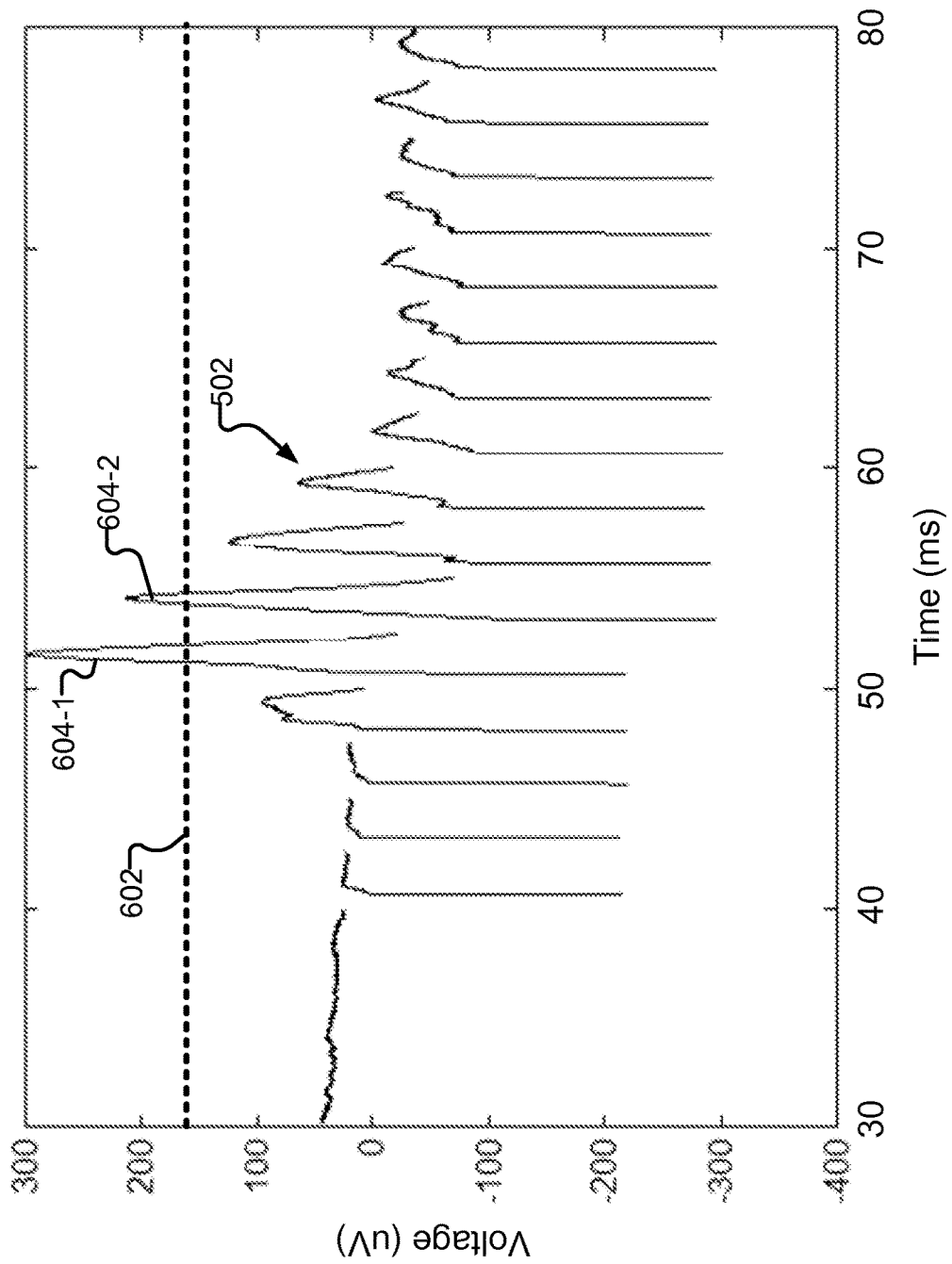
FIG. 6 shows an exemplary threshold level according to principles described herein.

To illustrate, FIG. 6 shows an exemplary threshold level 602 that may be set by EMG signal processing facility 206 (e.g., in response to one or more user input commands provided by a user of EMG response detection system 100). EMG signal processing facility 206 may compare voltage levels of individual peaks included in averaged EMG signal 502 to threshold level 602. If one or more (or any other predetermined number) of peaks have voltage levels above threshold level 602, EMG signal processing facility 502 may determine that an EMG response has been evoked by the stimulation events. To illustrate, in the example of FIG. 6, peaks 604-1 and 604-2 have voltage levels that are greater than threshold level 602. Hence, EMG signal processing facility 206 may determine that an EMG response has been evoked by the stimulation events corresponding to the EMG signals used to generate averaged EMG signal 502.

Returning to FIG. 2, EMG signal processing facility 206 may determine an asynchronous component of each of the recorded EMG signals in any suitable manner. For example, EMG signal processing facility 206 may determine an asynchronous component of each of the recorded EMG signals by first determining a synchronous component of each of the recorded EMG signals (e.g., as described above) and then removing the synchronous components from the recorded EMG signals. To illustrate, EMG signal processing facility 206 may determine an asynchronous component of each of the recorded EMG signals by generating an averaged EMG signal and then subtracting the averaged EMG signal from each of the recorded EMG signals.

Figure 7:
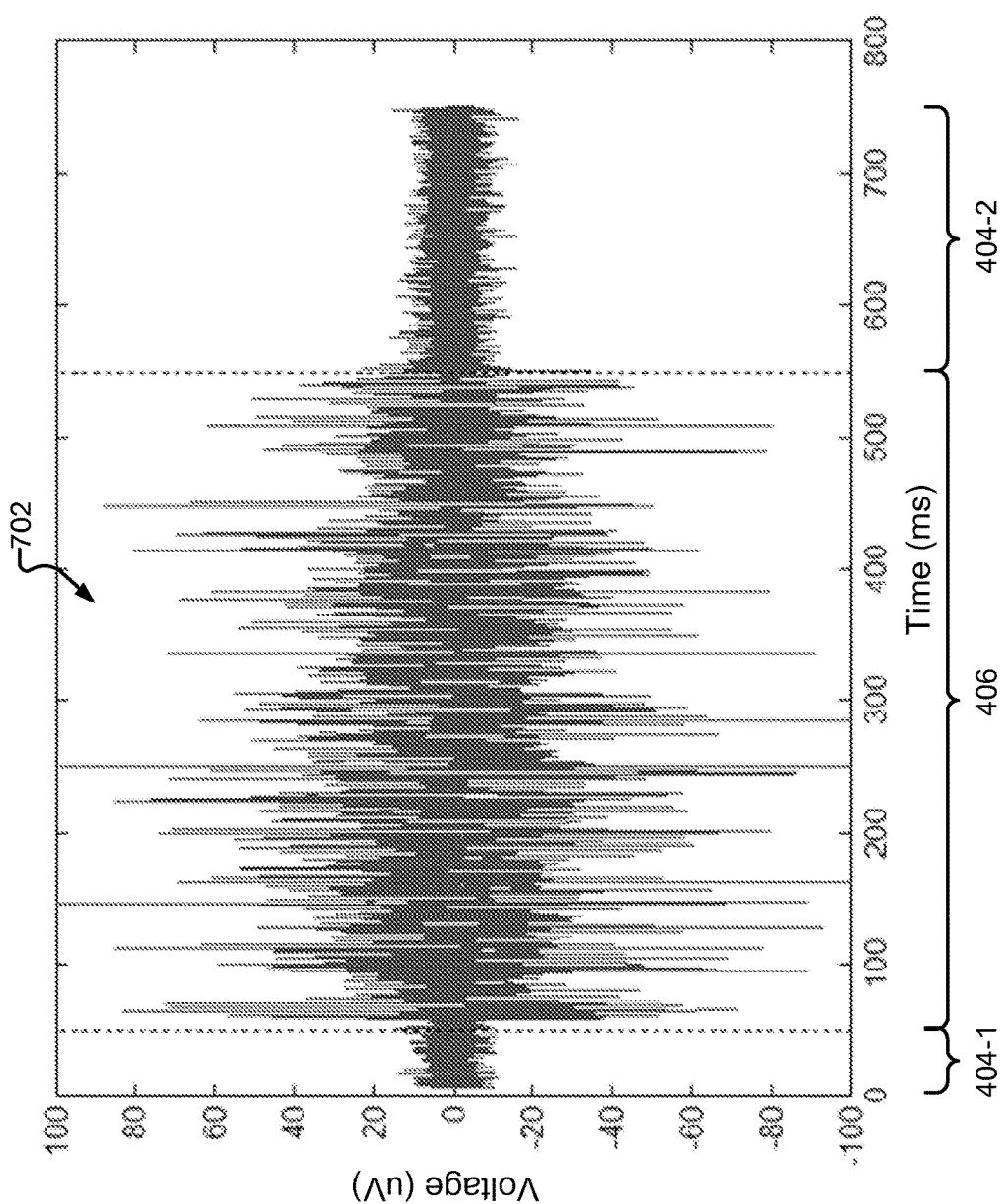
FIG. 7 illustrates an exemplary asynchronous component of an EMG signal according to principles described herein.

FIG. 7 illustrates an exemplary asynchronous component 702 of EMG signal 402. As shown, asynchronous component 702 may temporally correspond to EMG signal 402 in that it has the same baseline and response phases 404 and 406 as EMG signal 402.

In some examples, because the voltage level of asynchronous component 702 is relatively low, direct analysis of asynchronous component 702 may be unable to determine whether asynchronous component 702 includes an EMG response or whether asynchronous component 702 only includes noise and/or stimulus artifacts.

Hence, in some examples, EMG signal processing facility 206 may determine whether an EMG response is evoked by the stimulation events associated with each of the recorded EMG signals by determining and then comparing an amount of energy included in the response phases of the asynchronous components to an amount of energy included in the baseline phases of the asynchronous components. If the amount of energy contained within the response phases is greater than the amount of energy contained within the baseline phases by more than a predetermined threshold amount, EMG signal processing facility 206 may determine that an EMG response has been evoked by the stimulation events. Alternatively, if the amount of energy contained within the response phases is not greater than the amount of energy contained within the baseline phases by more than the predetermined threshold amount, EMG signal processing facility 206 may determine that an EMG response was not evoked by the stimulation events.

EMG signal processing facility 206 may determine the amount of energy included in the response phases of the asynchronous components and the amount of energy contained within the baseline phases of the asynchronous components in any suitable manner. For example, EMG signal processing facility 206 may utilize any suitable energy estimation or computation heuristic to determine the amount of energy included in each of the response and baseline phases.

Figure 8:
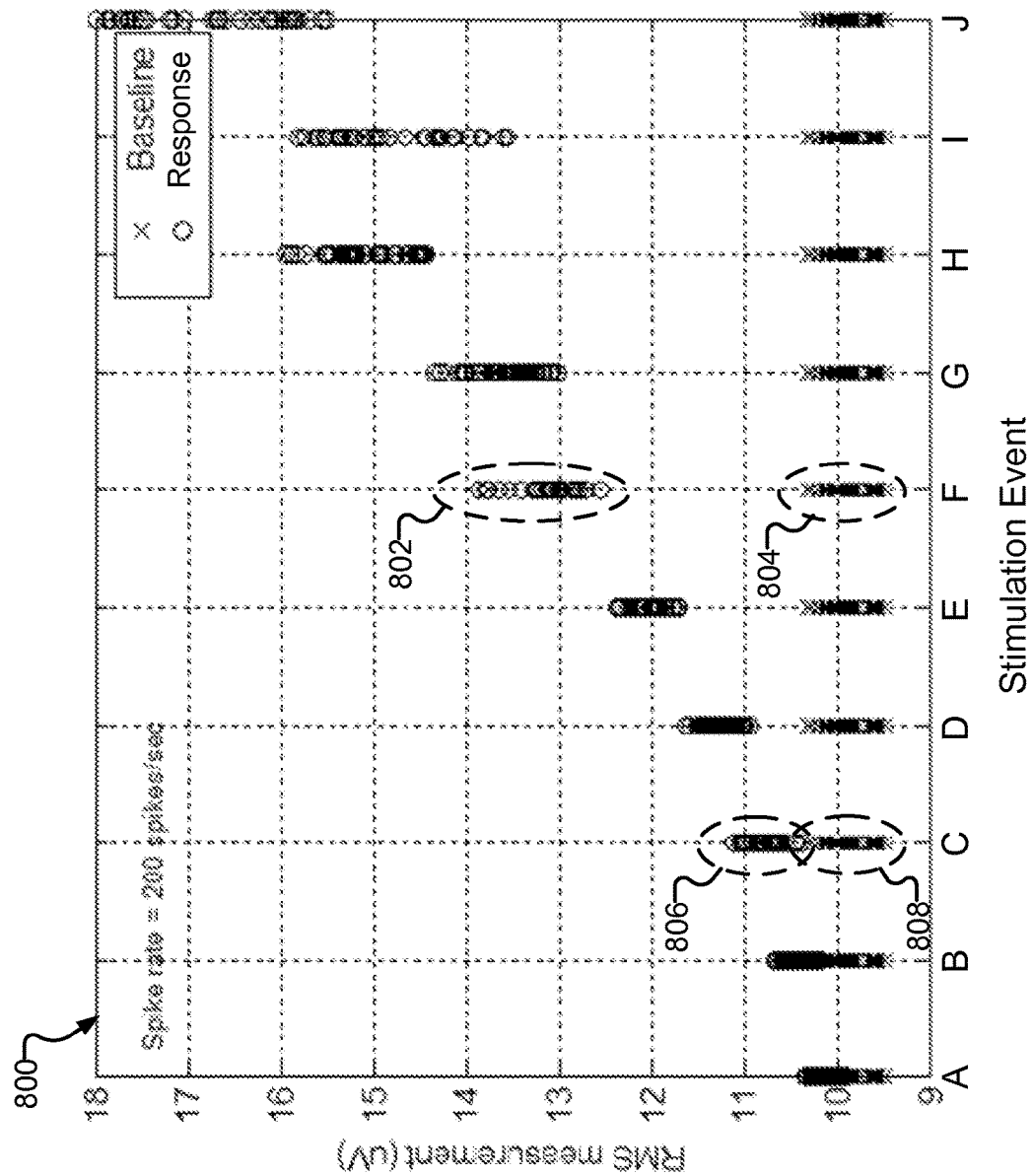
FIG. 8 shows a graph within which response phase energy levels and baseline phase energy levels for various sets of asynchronous components of recorded EMG signals have been plotted according to principles described herein.

Moreover, EMG signal processing facility 206 may compare the amount of energy included in the response phases of the asynchronous components to the amount of energy contained within the baseline phases of the asynchronous components in any suitable manner. For example, FIG. 8 shows a graph 800 within which response phase energy levels and baseline phase energy levels for various sets of asynchronous components of recorded EMG signals have been plotted. For illustrative purposes, response phase energy levels are represented in FIG. 8 by the symbol "○" and baseline phase energy levels are represented by the symbol "x".

As shown, the response and baseline phase energy levels represented in FIG. 8 are aligned with different stimulation events shown along the x-axis. For example, response phase energy levels included within group 802 and baseline phase energy levels included within group 804 correspond to a sequential presentation of a stimulation event labeled "F." Each response phase energy level included within group 802 represents an energy level within the response phase of a particular asynchronous component of a particular recorded EMG signal corresponding to a presentation of the stimulation event labeled "F." Likewise, each baseline phase energy level included within group 804 represents an energy level within the baseline phase of a particular asynchronous component of a particular recorded EMG signal corresponding to a presentation of the stimulation event labeled "F."

In some examples, the response phase energy levels associated with a particular stimulation event (e.g., the response phase energy levels included within group 802) may be averaged to determine an average response phase energy level for a particular set of asynchronous components. Likewise, the baseline phase energy levels associated with the particular stimulation event (e.g., the baseline phase energy levels included within group 804) may be averaged to determine an average baseline phase energy level for the same set of asynchronous components. The average response phase energy level may be compared to the average baseline phase energy level to determine if the average response phase level is greater than the average baseline phase energy level by more than a predetermined threshold amount. If it is, EMG signal processing facility 206 may determine that the stimulation event evoked an EMG response.

To illustrate, the average response phase energy level of the response phase energy levels included within group 802 may be determined to be greater than the average baseline phase energy level of the baseline phase energy levels included within group 804 by more than a predetermined threshold amount. Hence, EMG signal processing facility 206 may determine that the stimulation event labeled "F" evoked an EMG response. However, the average response phase energy level of the response phase energy levels included within group 806 may be determined to not be greater than the average baseline phase energy level of the baseline phase energy levels included within group 808 by more than a predetermined threshold amount. Hence, EMG signal processing facility 206 may determine that the stimulation event labeled "C" did not evoke an EMG response.

As illustrated in FIG. 8, the response phase energy levels for a particular set of asynchronous components may vary in energy level. Likewise, the baseline phase energy levels for a particular set of asynchronous components may vary in energy level. Hence, to ensure accurate results, it may be beneficial to utilize the asynchronous components of all of the recorded EMG signals to determine whether an EMG response has been evoked by a stimulation event. However, it will be recognized that in some situations (e.g., in situations where reduced processing time is desirable), fewer than all of the asynchronous components of the recorded EMG signals may be analyzed to determine whether an EMG response has been evoked by a stimulation event. For example, in some instances, only a single asynchronous component may be generated and used to determine whether an EMG response has been evoked by a stimulation event.

In some alternative examples, EMG signal processing facility 206 may utilize the asynchronous components of the recorded EMG signals to determine whether an EMG response is evoked by the stimulation events associated with each of the recorded EMG signals by determining an amount of energy contained in each of a plurality of discrete time-based phases of each of the asynchronous components, identifying a time-based trend with respect to the amount of energy contained within each of the discrete phases, and determining, based on the time-based trend, whether the EMG response is evoked by the stimulation events.

For example, EMG signal processing facility 206 may determine an amount of energy contained in ten ms segments of a plurality of asynchronous components. EMG signal processing facility 206 may determine that the energy level increases rapidly and then gradually decays across successive time-based segments. Based on this trend, EMG signal processing facility 206 may determine that an EMG response has been evoked by the stimulation events.

In some examples, EMG signal processing facility 206 may be further configured to filter out noise contained in each of the recorded EMG signals prior to determining the asynchronous components of each of the recorded EMG signals. For example, EMG signal processing facility 206 may filter out content that is not within a predetermined frequency range where the EMG response is expected to be. In this manner, EMG signal processing facility 206 may more readily determine whether an EMG response is contained within the asynchronous components.

Returning to FIG. 2, storage facility 208 may be configured to maintain EMG signal processing data 210 generated and/or utilized by recording facility 204 and/or EMG response processing facility 206. Storage facility 208 may be configured to maintain additional or alternative data as may serve a particular implementation.

Figure 9:
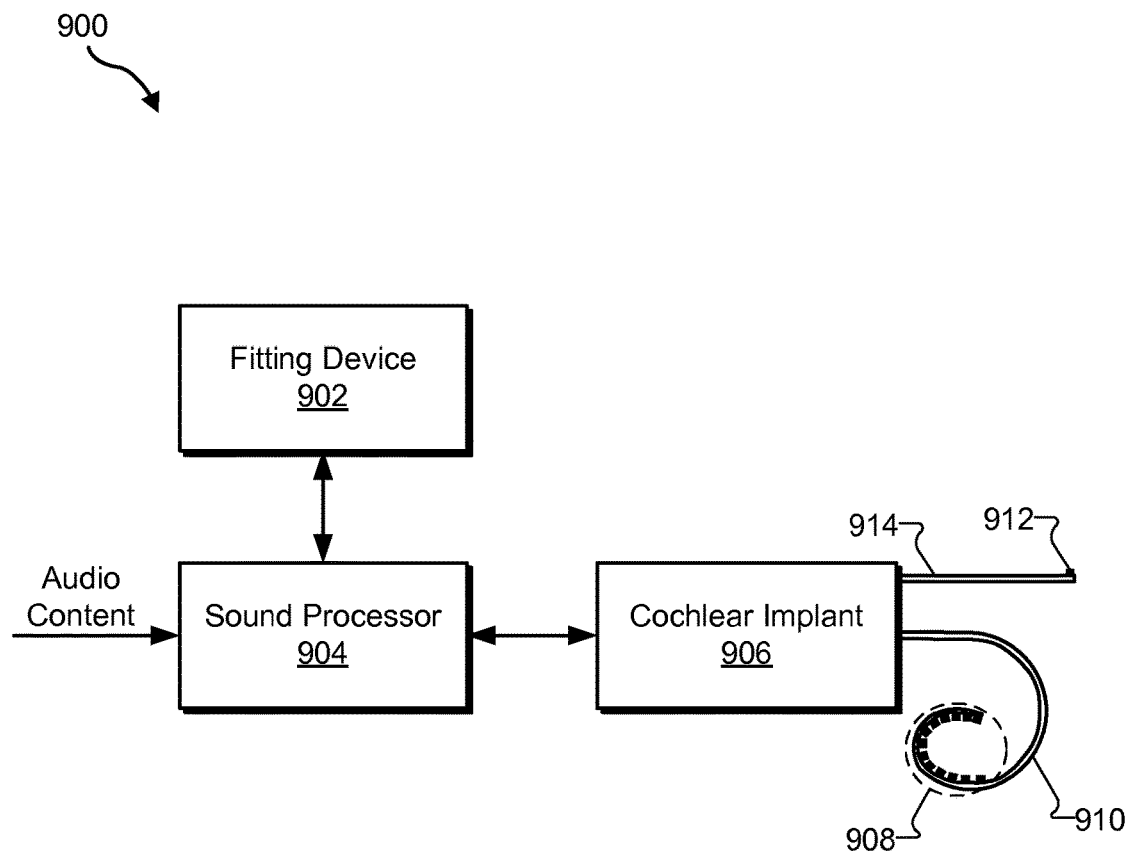
FIG. 9 illustrates an exemplary cochlear implant system implementation of the EMG response detection system and implantable stimulator shown in FIG. 1 according to principles described herein.

FIG. 9 illustrates an exemplary cochlear implant system implementation 900 of EMG response detection system 102 and implantable stimulator 104. As shown, implementation 900 includes a fitting device 902 communicatively coupled to a sound processor 904, which may in turn be communicatively coupled to a cochlear implant 906. EMG response detection system 102 may be at least partially implemented by fitting device 902 and/or sound processor 904. Implantable stimulator 104 may be at least partially implemented by cochlear implant 906.

Fitting device 902 may be implemented by any suitable combination of computing and communication devices including, but not limited to, a fitting station, an electromyograph, a personal computer, a laptop computer, a handheld device, a mobile device (e.g., a mobile phone), and/or any other suitable component as may serve a particular implementation. In some examples, fitting device 902 may provide one or more graphical user interfaces ("GUIs") with which a clinician or other user may interface in order to fit sound processor 904 and cochlear implant 906 (which, together, may be referred to as a "cochlear implant system") to a patient.

Sound processor 904 may include any suitable device configured to process audio content (e.g., one or more audio signals) presented to a patient and direct cochlear implant 906 to apply electrical stimulation representative of the audio content to the auditory nerve of the patient by way of one or more electrodes 908 disposed on a lead 910 configured to be disposed within the cochlea of the patient. Sound processor 904 may be implemented by a behind-the-ear ("BTE") unit, a body worn device, a portable speech processor ("PSP"), an electro-acoustic stimulation device ("EAS device"), and/or any other type of sound processing unit as may serve a particular implementation.

Cochlear implant 906 may include any suitable auditory prosthesis configured to be at least partially (e.g., fully) implanted within a patient as may serve a particular implementation. Sound processor 904 and cochlear implant 906 may communicate by way of any suitable wired or wireless communication channel.

In some examples, as shown in FIG. 9, a recording electrode 912 disposed on a lead 914 may be communicatively coupled to cochlear implant 906. Recording electrode 912 may be configured to be implanted within the stapedius muscle of the patient. In this configuration, recording electrode 912 may be used to detect stapedius muscle activity, which may include one or more stapedius reflexes.

Figure 10:
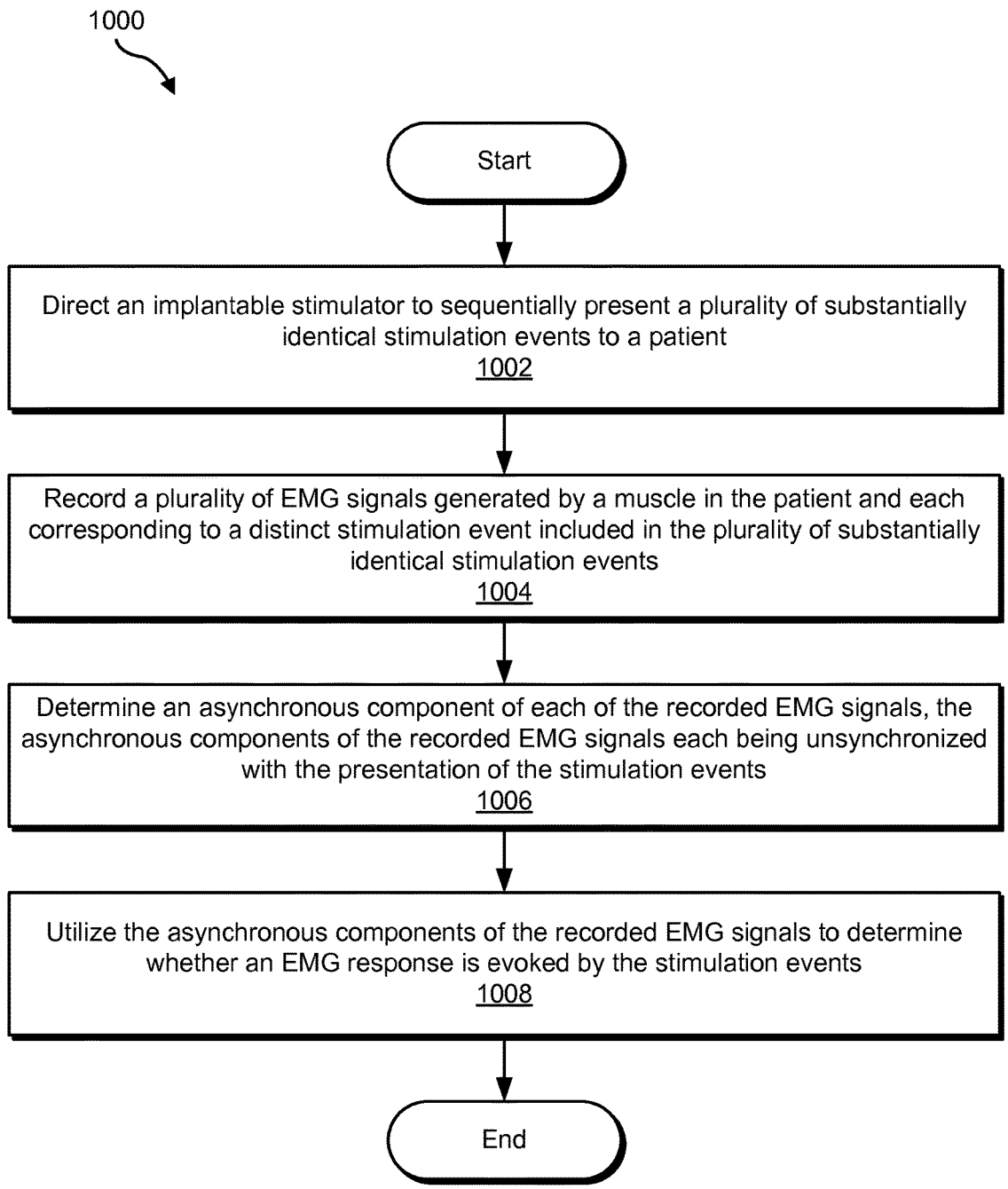
FIG. 10 illustrates an exemplary EMG response detection method according to principles described herein.

FIG. 10 illustrates an exemplary EMG response detection method 1000. While FIG. 10 illustrates exemplary steps according to one embodiment, other embodiments may omit, add to, reorder, and/or modify any of the steps shown in FIG. 10. One or more of the steps shown in FIG. 10 may be performed by EMG response detection system 102 and/or any implementation thereof.

In step 1002, an EMG response detection system directs an implantable stimulator to sequentially present a plurality of substantially identical stimulation events to a patient. Step 1002 may be performed in any of the ways described herein.

In step 1004, the EMG response detection system records a plurality of EMG signals generated by a muscle in the patient and each corresponding to a distinct stimulation event included in the plurality of substantially identical stimulation events. Step 1004 may be performed in any of the ways described herein.

In step 1006, the EMG response detection system determines an asynchronous component of each of the recorded EMG signals, the asynchronous components of the recorded EMG signals each being unsynchronized with the presentation of the stimulation events. Step 1006 may be performed in any of the ways described herein.

In step 1008, the EMG response detection system utilizes the asynchronous components of the recorded EMG signals to determine whether an EMG response is evoked by the stimulation events. Step 1008 may be performed in any of the ways described herein.

Figure 11:
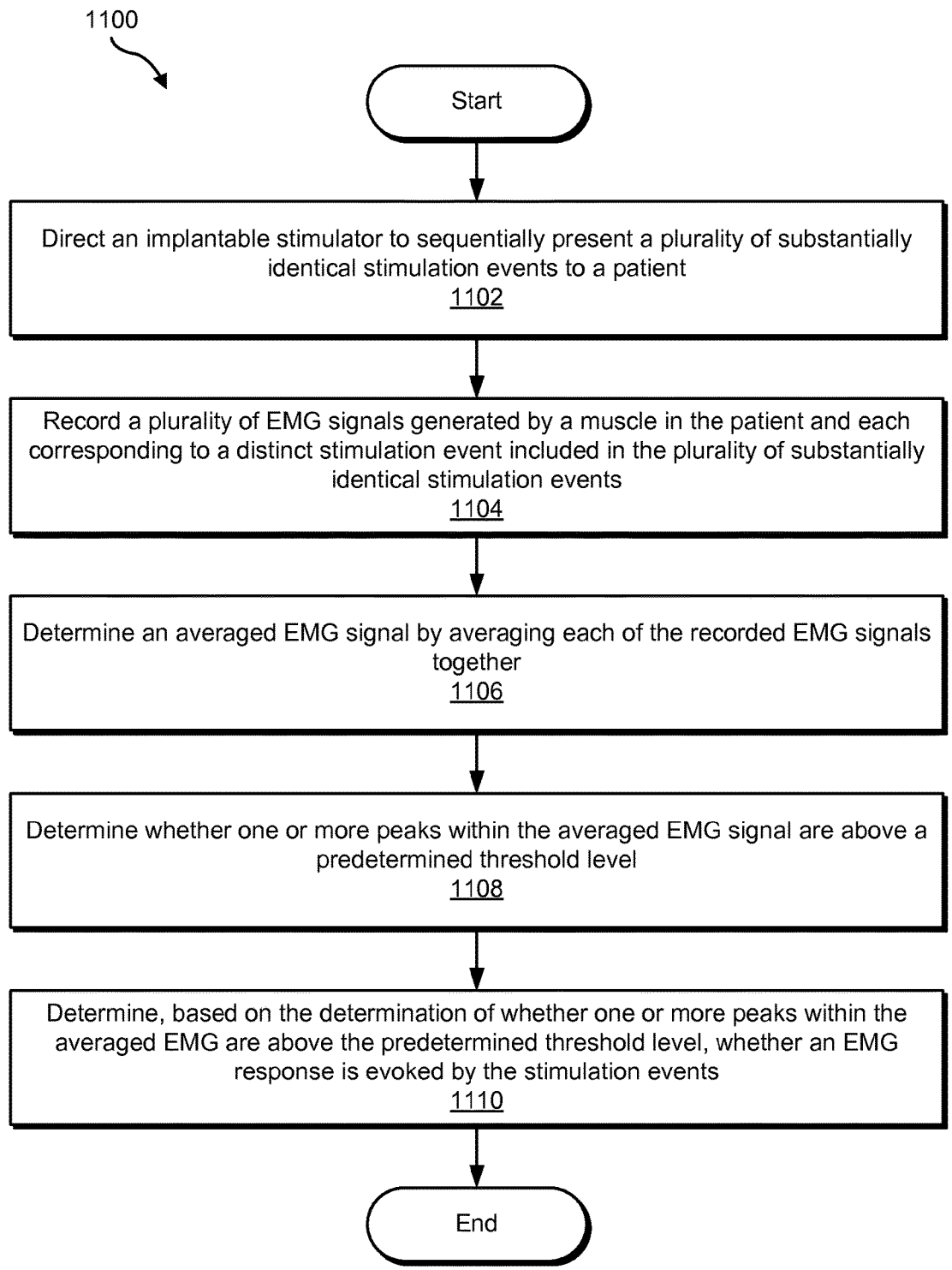
FIG. 11 illustrates another exemplary EMG response detection method according to principles described herein.

FIG. 11 illustrates another exemplary EMG response detection method 1100. While FIG. 11 illustrates exemplary steps according to one embodiment, other embodiments may omit, add to, reorder, and/or modify any of the steps shown in FIG. 11. One or more of the steps shown in FIG. 11 may be performed by EMG response detection system 102 and/or any implementation thereof.

In step 1102, an EMG response detection system directs an implantable stimulator to sequentially present a plurality of substantially identical stimulation events to a patient. Step 1102 may be performed in any of the ways described herein.

In step 1104, the EMG response detection system records a plurality of EMG signals generated by a muscle in the patient and each corresponding to a distinct stimulation event included in the plurality of substantially identical stimulation events. Step 1104 may be performed in any of the ways described herein.

In step 1106, the EMG response detection system determines an averaged EMG signal by averaging each of the recorded EMG signals together. Step 1106 may be performed in any of the ways described herein.

In step 1108, the EMG response detection system determines whether one or more peaks within the averaged EMG signal are above a predetermined threshold level. Step 1108 may be performed in any of the ways described herein.

In step 1110, the EMG response detection system determines, based on the determination of whether one or more peaks within the averaged EMG are above the predetermined threshold level, whether an EMG response is evoked by the stimulation events. Step 1110 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 12:
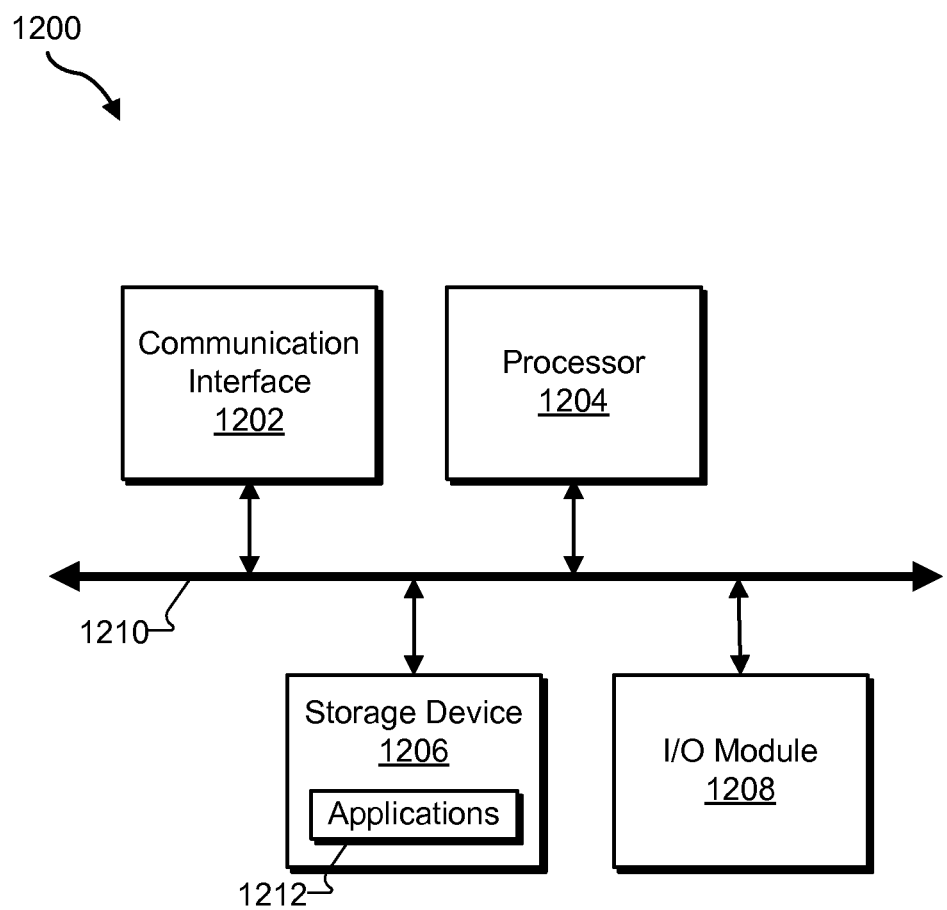
FIG. 12 illustrates an exemplary computing device according to principles described herein.

FIG. 12 illustrates an exemplary computing device 1200 that may be configured to perform one or more of the processes described herein. As shown in FIG. 12, computing device 1200 may include a communication interface 1202, a processor 1204, a storage device 1206, and an input/output ("I/O") module 1208 communicatively connected via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1206. For example, data representative of one or more executable applications 1212 configured to direct processor 1204 to perform any of the operations described herein may be stored within storage device 1206. In some examples, data may be arranged in one or more databases residing within storage device 1206.

I/O module 1208 may be configured to receive user input and provide user output and may include any hardware, firmware, software, or combination thereof supportive of input and output capabilities. For example, I/O module 1208 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1208 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1200. For example, one or more applications 1212 residing within storage device 1206 may be configured to direct processor 1204 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   at least one physical computing device configured to
   direct an implantable stimulator to sequentially present a plurality of substantially identical stimulation events to a patient;
   record a plurality of electromyography ("EMG") signals generated by a muscle in the patient and each corresponding to a presentation of a particular stimulation event included in the plurality of substantially identical stimulation events;
   determine an asynchronous component of each of the recorded EMG signals, the asynchronous components of the recorded EMG signals each being unsynchronized with the sequential presentation of the stimulation events;
   determine an amount of energy contained within each of a plurality of phases of each of the asynchronous components;

analyze the amounts of energy contained within each of the plurality of phases of each of the asynchronous components; and determine, based on the analysis of the amounts of energy, whether an EMG response is evoked by the stimulation events.

2. The system of claim 1, wherein the at least one physical computing device is configured to determine the asynchronous component of each of the recorded EMG signals by:

determining a synchronous component of each of the recorded EMG signals, the synchronous components of the recorded EMG signals being synchronized with the sequential presentation of the stimulation events and each representing a synchronous component common to all of the recorded EMG signals; and removing the synchronous components from each of the recorded EMG signals to leave only the asynchronous component of each of the recorded EMG signals.

3. The system of claim 2, wherein the at least one physical computing device is configured to:

determine the synchronous components of the recorded EMG signals by averaging each of the recorded EMG signals together, the averaging resulting in an averaged EMG signal representative of the synchronous component common to all of the recorded EMG signals; and remove the synchronous components from each of the recorded EMG signals by subtracting the averaged EMG signal from each of the recorded EMG signals.

4. The system of claim 1, wherein the at least one physical computing device is configured to direct the implantable stimulator to sequentially present the plurality of substantially identical stimulation events to the patient by directing the implantable stimulator to sequentially present a plurality of substantially identical electrical stimulation pulse trains temporally spaced one from another by a predetermined time period.

5. The system of claim 1, wherein the at least one physical computing device is configured to direct the implantable stimulator to sequentially present the plurality of substantially identical stimulation events to the patient by directing a cochlear implant to sequentially apply the substantially identical stimulation events to one or more stimulation sites within a cochlea of the patient by way of one or more electrodes disposed within the cochlea.

6. The system of claim 5, wherein the muscle is a stapedius muscle within the patient and wherein the EMG response is a stapedius reflex.

7. The system of claim 5, wherein the at least one physical computing device is configured to record the plurality of EMG signals using an electrode that is in physical communication with the muscle.

8. The system of claim 1, wherein the plurality of phases included within each of the asynchronous components includes a baseline phase corresponding to a time period during which an occurrence of the EMG response in response to the stimulation events is not possible and a response phase corresponding to a time period during which an occurrence of the EMG response in response to the stimulation events is possible.

9. The system of claim 8, wherein the time period corresponding to the baseline phase of an asynchronous component of a particular EMG signal comprises at least one of a time period prior to the presentation of the stimulation event and a time period that begins a predetermined amount of time subsequent to the presentation of the stimulation event.

10. The system of claim 8, wherein the time period corresponding to the response phase of an asynchronous component of a particular EMG signal comprises a time period during which the stimulation event is presented.

11. The system of claim 8, wherein the at least one physical computing device is configured to:

determine the amount of energy contained within each of the plurality of phases of each of the asynchronous components by:

determining an amount of energy contained within the response phase of the asynchronous component of each EMG signal included in the plurality of EMG signals, and determining an amount of energy contained within the baseline phase of the asynchronous component of each EMG signal included in the plurality of EMG signals; and determine whether the EMG response is evoked by the stimulation events based on the analysis of the amounts of energy by comparing the amount of energy contained within the response phases to the amount of energy contained within the baseline phases.

12. The system of claim 11, wherein, if the comparison determines that the amount of energy contained within the response phases is greater than the amount of energy contained within the baseline phases by more than a predetermined threshold amount, the at least one physical computing device is configured to determine that the EMG response is evoked by the stimulation events.

13. The system of claim 12, wherein, if the comparison determines that the amount of energy contained within the response phases is not greater than the amount of energy contained within the baseline phases by more than the predetermined threshold amount, the at least one physical computing device is configured to determine that the EMG response is not evoked by the stimulation events.

14. The system of claim 1, wherein the at least one physical computing device is configured to:

determine the amount of energy contained within each of the plurality of phases of each of the asynchronous components by determining an amount of energy contained in each of a plurality of discrete time-based phases of each of the asynchronous components; and determine whether the EMG response is evoked by the stimulation events based on the analysis of the amounts of energy by:

identifying a time-based trend with respect to the amount of energy contained within each of the discrete phases; and determining, based on the time-based trend, whether the EMG response is evoked by the stimulation events.

15. The system of claim 1, wherein the at least one physical computing device is further configured to filter out noise contained in each of the recorded EMG signals prior to determining the asynchronous components of each of the recorded EMG signals.

16. A method comprising:

directing, by an electromyography ("EMG") response detection system, an implantable stimulator to sequentially present a plurality of substantially identical stimulation events to a patient;

recording, by the EMG response detection system, a plurality of EMG signals generated by a muscle in the patient and each corresponding to a distinct stimulation event included in the plurality of substantially identical stimulation events;

determining, by the EMG response detection system, an asynchronous component of each of the recorded EMG signals, the asynchronous components of the recorded EMG signals each being unsynchronized with the sequential presentation of the stimulation events;

determining, by the EMG response detection system, an amount of energy contained within each of a plurality of phases of each of the asynchronous components;

analyzing, by the EMG response detection system, the amounts of energy contained within each of the plurality of phases of each of the asynchronous components; and determining, by the EMG response detection system based on the analysis of the amounts of energy, whether an EMG response is evoked by the stimulation events.

17. The method of claim 16, wherein the plurality of phases included within each of the asynchronous components includes a baseline phase corresponding to a time period during which an occurrence of the EMG response in response to the stimulation events is not possible and a response phase corresponding to a time period during which an occurrence of the EMG response in response to the stimulation events is possible.

18. The method of claim 17, wherein:

the determining of the amount of energy contained within each of the plurality of phases of each of the asynchronous components includes:
  determining an amount of energy contained within the response phase of the asynchronous component of each EMG signal included in the plurality of EMG signals, and
  determining an amount of energy contained within the baseline phase of the asynchronous component of each EMG signal included in the plurality of EMG signals; and the determining of whether the EMG response is evoked by the stimulation events based on the analysis of the amounts of energy includes comparing the amount of energy contained within the response phases to the amount of energy contained within the baseline phases.

19. The method of claim 18, wherein:

if the comparison determines that the amount of energy contained within the response phases is greater than the amount of energy contained within the baseline phases by more than a predetermined threshold amount, the EMG response is determined to be evoked by the stimulation events; and if the comparison determines that the amount of energy contained within the response phases is not greater than the amount of energy contained within the baseline phases by more than the predetermined threshold amount, the EMG response is determined to not be evoked by the stimulation events.

20. The method of claim 16, wherein:

the determining of the amount of energy contained within each of the plurality of phases of each of the asynchronous components includes determining an amount of energy contained in each of a plurality of discrete time-based phases of each of the asynchronous components; and the determining of whether the EMG response is evoked by the stimulation events based on the analysis of the amounts of energy includes
  identifying a time-based trend with respect to the amount of energy contained within each of the discrete phases, and
  determining, based on the time-based trend, whether the EMG response is evoked by the stimulation events.

* * * * *